United States Patent [19] [11] 3,933,802
Ferrini et al. [45] Jan. 20, 1976

[54] SULPHAMOYLBENZOIC ACID AMIDES

[75] Inventors: Pier Giorgio Ferrini, Binningen; Georges Haas; Alberto Rossi, both of Oberwil, all of Switzerland

[73] Assignee: Ciba-Geigy Corporation, Ardsley, N.Y.

[22] Filed: May 22, 1974

[21] Appl. No.: 472,333

[30] Foreign Application Priority Data
May 28, 1973 Switzerland............... 7643/73
Apr. 1, 1974 Switzerland............... 4507/74

[52] U.S. Cl................ 260/239.7; 424/229
[51] Int. Cl.² ...........C07D 237/00; C07D 239/00; C07D 241/00; C07D 251/00
[58] Field of Search........ 260/239.6, 239.7, 239.75, 260/239.65; 424/229

[56] References Cited
UNITED STATES PATENTS
2,910,488 10/1959 Novello............... 260/239.6
3,444,177 5/1969 Schmidt et al......... 260/239.7

FOREIGN PATENTS OR APPLICATIONS
2,598 M 5/1963 France............... 260/239.6
2,001,158 7/1970 Germany Primary Examiner—Sam Rosen
Assistant Examiner—D. W. Robinson
Attorney, Agent, or Firm—Joseph G. Kolodny; John J. Maitner; Theodore O. Groeger

[57] ABSTRACT

New 2-amino-5-sulphamoylbenzoic acid amide of the general formula

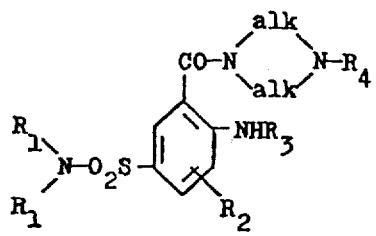

wherein $R_1$ denotes lower alkyl, $R_2$ denotes hydrogen, halogen, trifluoromethyl, lower alkyl or lower alkoxy, $R_3$ denotes hydrogen, hydroxyl or lower alkyl, $R_4$ denotes acyl and alk denotes lower 1,2-alkylene or 1,3-alkylene or a therapeutically acceptable acid addition salt thereof are usefull as mild analgesics with an anti-inflammatory component of action.

16 Claims, No Drawings

NEW SULPHAMOYLBENZOIC ACID AMIDES

The invention relates to new 2-amino-5-sulphamoylbenzoic acid amides of the general formula

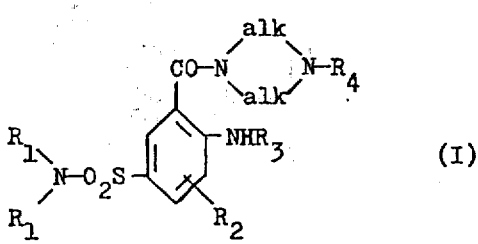

wherein $R_1$ denotes lower alkyl, $R_2$ denotes hydrogen, halogen, trifluoromethyl, lower alkyl or lower alkoxy, $R_3$ denotes hydrogen, hydroxyl or lower alkyl, $R_4$ denotes acyl and alk denotes lower 1,2-alkylene or 1,3-alkylene, and processes for their manufacture.

The radicals $R_1$ and alk can in each case be identical or different.

Lower alkyl $R_1$, $R_2$ and $R_3$ contains in particular 1 to 7 C atoms, above all 1 to 4 C atoms, and is therefore in particular heptyl, hexyl or pentyl, which can be straight-chain or branched and linked in any position, or, above all, n-butyl, sec.-butyl, tert.-butyl, isobutyl, isopropyl or n-propyl or especially ethyl or methyl.

Halogen $R_2$ is in particular fluorine, bromine or above all chlorine.

Lower alkoxy $R_2$ contains in particular 1 to 7 C atoms, above all 1 to 4 C atoms, and is therefore in particular heptyloxy, hexyloxy or pentoxy, which can be straight chain or branched and linked in any position, or above all n-butoxy, sec.-butoxy, tert.-butoxy, isobutoxy, isopropoxy or n-propoxy, ethoxy or methoxy.

Acyl $R_4$ is in particular acyl of the formula —COR or —COOR wherein R denotes lower alkyl, lower alkenyl or aryl-lower alkyl.

Lower alkyl R contains in particular 1 to 7 C atoms, above all 1 to 4 C atoms, and is above all one of the lower alkyl groups mentioned for $R_1$, $R_2$ and $R_3$.

Lower alkenyl R contains in particular 2 to 4 C atoms, above all 3 or 4 C atoms, and is especially allyl or methallyl.

Aryl-lower alkyl R is in particular phenyl-lower alkyl with 1 to 4 C atoms in the alkyl part, which is optionally substituted in the phenyl part by lower alkyl, lower alkoxy, halogen, trifluoromethyl and/or nitro, above all benzyl or phenylethyl which are optionally substituted as indicated.

The radicals alk can be straight-chain or branched and can contain, where appropriate, 1 to 7 C atoms, particularly 1 to 4 C atoms, in the side chain. 3-Methylbutylene-1,3 and isobutylene-1,3 and above all isobutylene-1,2, butylene-2,3 and particularly propylene-1,3 and especially butylene-1,2, propylene-1,2 and ethylene should be mentioned as examples.

The new 2-amino-5-sulphamoylbenzoic acid amides possess valuable pharmacological properties. Thus they exhibit, in particular, a distict anti-inflammatory action, as can be shown, for example, in the turpentine-pleuritis test on rats on peroral adminsitration of a dose of 10 to 300 mg/kg in each case, and above all a distinct antinociceptive (analgesic) action, as can be shown, for example, in the acetic acid writhing test on mice on peroral administration of a dose of 100 to 300 mg/kg in each case. They are also distinguished by a comparatively low toxicity, as can be shown, for example, on peroral administration to rats. The new 2-amino-5-sulphamoylbenzoic acid amides therefore are usefull as mild analgesics with an anti-inflammatory component of action.

The invention relates above all to those 2-amino-5-sulphamoylbenzoic acid amides of the formula I wherein $R_1$ denotes identical lower alkyl groups with 1 to 4 C atoms, such as methyl or ethyl, $R_2$ denotes hydrogen, lower alkyl or lower alkoxy with up to 4 carbon atoms, or halogen up to atomic number 17, such as fluorine or chlorine, $R_3$ denotes hydrogen, hydroxyl or lower alkyl with 1 to 4 C atoms, such as isopropyl, n-propyl or above all ethyl or methyl, $R_4$ denotes a group of the formula —COOR' or —COR' wherein R' denotes lower alkyl with 1 to 4 C atoms, such as isobutyl, n-butyl, isopropyl, n-propyl, ethyl or methyl, lower alkenyl with 3 or 4 C atoms, such as allyl or methallyl, or phenyl, benzyl or phenylethyl which is optionally monosubstituted or disubstituted in the phenyl part by lower alkyl or lower alkoxy with 1 to 4 C atoms in each case, such as methyl or methoxy, halogen up to atomic number 17, such as chlorine, or nitro, and alk denotes 1,2-alkylene with 2-4 C atoms, such as butylene-2,3 or above all butylene-1,2, propylene-1,2 or ethylene.

However, the invention relates particularly to those 5-sulphamoylanthranilic acid amides of the formula I wherein $R_1$ is methyl, $R_2$ is chlorine, methoxy, methyl or above all hydrogen, $R_3$ is hydrogen or lower alkyl with 1 to 4 C atoms, such as ethyl or methyl, $R_4$ denotes a group of the formula —COOR' or —COR' wherein R' is lower alkyl with 1 to 4 C atoms, such as isobutyl, n-butyl, isopropyl, n-propyl, ethyl or methyl, lower alkenyl with 3 or 4 C atoms, such as allyl or methallyl, or phenyl, benzyl or phenylethyl which is optionally monosubstituted or disubstituted in the phenyl part by lower alkyl or lower alkoxy with 1 to 4 C atoms in each case, such as methyl or methoxy, halogen up to atomic number 17, such as chlorine, or nitro, and alk denotes 1,2-alkylene with 2 to 4 C atoms, such as butylene-2,3, butylene-1,2, propylene-1,2 or above all ethylene.

The invention relates very particularly, however, to those of the abovementioned 5-sulphamoylanthranilic acid amides of the formula I wherein $R_1$ is methyl, $R_2$ is hydrogen, $R_3$ is hydrogen, ethyl or methyl, $R_4$ is a group of the formula —COOR'' or —COR'' wherein R'' denotes lower alkyl with 1 to 4 C atoms, allyl, phenyl or benzyl which is optionally nitrated, for example in the p-position, and alk is propylene-1,2 or above all ethylene.

The invention relates especially, however, to those of the abovementioned 5-sulphamoylanthranilic acid amides of the formula I wherein $R_1$ is methyl, $R_2$ is hydrogen, $R_3$ is hydrogen or ethyl, $R_4$ is a group of the formula —COOR'' wherein R'' denotes lower alkyl with 1 to 4 C atoms, allyl or benzyl which is optionally nitrated, especially in the p-position, and alk is ethylene, wherein 1-[5-(dimethylsulphamoyl)-anthraniloyl]-4-ethoxycarbonylpiperazine in particular should be singled out.

The new 2-amino-5-sulphamoylbenzoic acid amides can be obtained by processes which are in themselves known.

Thus, for example, it is possible to prepare 2-amino-5-sulphamoylbenzoic acid amides of the formula I wherein $R_3$ is hydrogen or hydroxy, by reducing the nitro group in a 2-nitro-5-sulphamoylbenzoic acid amide of the formula II

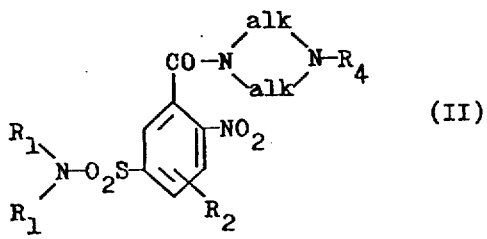

(II)

wherein $R_1$, $R_2$, $R_4$ and alk have the indicated meanings.

The reduction of the nitro group can be carried out in a manner which is in itself known and particularly in a manner which is described for analogous reactions, such as by means of nascent hydrogen, produced, for example, by the action of a strong acid, such as a hydrogen halide acid, above all hydrochloric acid, or sulphuric acid or a lower aliphatic carboxylic acid, such as acetic acid, on base metals, such as iron, zinc, magnesium or aluminium, or by means of a suitable light metal hydride, such as lithium borohydride or above all sulphurised sodium borohydride, or by means of hydrogen in the presence of a suitable hydrogenation catalyst, such as palladium on charcoal, platinum oxide or Raney nickel or Rupe nickel, in a solvent which is inert under the conditions of hydrogenation, if necessary at elevated pressure and/or elevated temperature.

In the course thereof, depending on the reaction conditions, the nitro group can be reduced either to the hydroxylamino group or through to the primary amino group. Thus 2-hydroxylamino-5-sulphamoylbenzoic acid amides are predominantly obtained in the reduction with nascent hydrogen in neutral or weakly acid solution and in the reaction with hydrogen at room temperature and normal pressure in the presence of 10% strength palladium/charcoal, breaking off the hydrogenation after 2 equivalents of hydrogen have been taken up. In contrast, 5-sulphamoylanthranilic acid amides are obtained under drastic conditions, for example with nascent hydrogen in mineral acid solution or with hydrogen at elevated pressure and/or elevated temperature or, above all, when using Rupe nickel as the catalyst.

However, it is also possible to prepare the new 2-amino-5-sulphamoylbenzoic acid amides by reacting a 5-sulphamoylisatoic acid anhydride of the formula IIIa

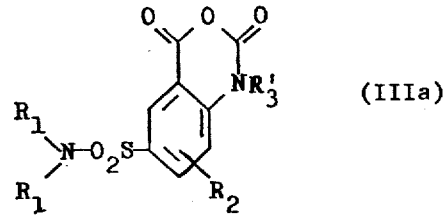

(IIIa)

wherein $R_1$ and $R_2$ have the indicated meanings and $R_3'$ denotes hydrogen or lower alkyl, with an amine of the formula IV

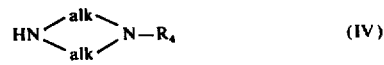

(IV)

wherein alk and $R_4$ have the indicated meanings to yield an optionally N-lower alkylated 5-sulphamoylanthranilic acid amide.

The reaction with the amine of the formula IV can be carried out in a manner which is in itself known, if necessary in the presence of a solvent and/or a condensation agent, especially a basic condensation agent, and advantageously at an elevated temperature.

In resulting 2-amino-5-sulphamoylbenzoic acid amides, substituents can be introduced, modified and split off within the scope of the definition of the end products.

Thus it is possible, for example, to introduce halogen $R_2$ in the customary manner into resulting 2-amino-5-sulphamoylbenzoic acid amides in which $R_2$ is hydrogen, for example by reaction with chlorine or bromine, preferably in the presence of a catalyst, such a iron-(III) chloride, or by means of N-chlorosuccinimide. On the other hand, halogen $R_2$ can be replaced by hydrogen $R_2$ in the customary manner, for example with hydrogen in the presence of a catalyst, such as palladium, platinum oxide or Raney nickel, or by the action of a trialkyltin hydride, such as triethyltin hydride. It is also possible to introduce trifluoromethyl $R_2$ in the customary manner, for example by reaction with trifluoroiodomethane in the presence of metals such as copper powder. In addition, it is possible to introduce lower alkyl $R_2$ in the customary manner, for example by reaction with a lower alkyl halide, advantageously in the presence of a catalyst, such as a metal halide, for example aluminum chloride or aluminium bromide.

It is also possible to introduce lower alkyl groups $R_3$ in the customary manner into resulting 5-sulphamoylanthranilic acid amides of the formula I wherein $R_3$ is hydrogen, for example by reaction with a customary alkylating agent, such as a reactive ester of an alcohol of the formula $R_3$—OH, for example with an organic sulphonic acid, such as benzenesulphonic acid, p-bromobenzenesulphonic acid, toluenesulphonic acid or methanesulphonic acid, or with an inorganic sulphonic acid, such as fluorosulphonic acid, or with a strong inorganic acid, such as hydrochloric acid, hydrobromic acid or hydriodic acid or sulphuric acid, or by reaction with a corresponding onium salt, for example a tri-lower alkyl oxonium tetrafluoroborate or a di-lower alkyl iodonium iodide.

The reactions with reactive esters are preferably carried out in the presence of an acid-binding agent, such as a tertiary organic base, for example ethyldiisopropylamine, pyridine or quinoline, or an inorganic base, such as an alkali metal hydroxide or an alkaline earth metal hydroxide or an alkali metal carbonate, for example sodium hydroxide, potassium hydroxide or calcium hydroxide or potassium carbonate or sodium carbonate. The alkylation procedures described above are preferably carried out in an inert organic solvent, such as a hydrocarbon, for example benzene, toluene or xylene, or, in the case of the reaction with reactive esters for example, in an ether, such as diethyl ether, tetrahydrofurane or dioxane, or, in the case of the reaction with onium salts, in a chlorinated or nitrated hydrocarbon, for example methylene chloride, tetrachloromethane, nitrobenzene or nitromethane.

The alkylation can, however, also be carried out by reaction with a corresponding oxo compound, for example with a corresponding aldehyde or ketone, under reducing conditions, for example in the presence of hydrogen and appropriately in the presence of a hydrogenation catalyst, such as a palladium, platinum or nickel catalyst, for example palladium on charcoal or calcium carbonate, or platinum oxide or Raney nickel, under normal or, preferably, elevated pressure, or in the presence of a hydrogen donor, such as a di-light metal hydride, for example lithium aluminium hydride, sodium cyanoborohydride or sodium borohydride, in each case advantageously in a solvent which is inert under the conditions of the reduction. For example, it is particuarly advantageous to introduce a methyl group by heating the compound to be methylated with a mixture of formaldehyde and formic acid, for example for 1 to 24 hours at temperature between approx. 60° and 120°C, preferably at the reflux temperature of the reaction mixture. The formaldehyde can also be employed in the form of a formaldehyde donor, for example as paraformaldehyde or as an aqueous solution. In a preferred embodiment, for example, paraformaldehyde in 90% strength formic acid or approximately 30% strength aqueous formalin solution/80% strength formic acid is used.

Resulting 2-hydroxylamino-5-sulphamoylbenzoic acids can also be reduced in the customary manner to give the corresponding 5-sulphamoylanthranilic acid amides, for example by the action of sufficiently strong reducing agents, for example by means of nascent hydrogen, produced, for example, by the action of a strong acid, such as a hydrogen halide acid, above all hydrochloric acid, sulphuric acid or a lower aliphatic carboxylic acid, such as acetic acid, on base metals, such as iron, zinc, magnesium or aluminium, or by means of a suitable light metal hydride, such as lithium borohydride or above all sulphurised sodium borohydride, or by means of hydrogen in the presence of a suitable hydrogenation catalyst, for example Rupe nickel or Raney nickel or platinum oxide, preferably at elevated pressure.

In the abovementioned reductions, care must be taken where appropriate that other reducible groups are not attacked. Care must thus be taken, especially in the reduction with Raney nickel and hydrogen, that halogen atoms which may be present, linked to aromatic rings, are not replaced by hydrogen. Where appropriate, the absorption of hydrogen should be followed volumetrically and the hydrogenation should be discontinued after the absorption of the calculated quantity. Moreover, in all reductions, particularly with complex hydrides, consideration must be given to the 5-(di-lower alkyl sulphamoyl)-group and to the acyl group $R_4$.

The reactions mentioned can optionally be carried out simultaneously or successively and in any desired sequence.

The reactions mentioned are carried out in the customary manner in the presence or absence of diluents, condensation agents and/or catalytic agents, at reduced, normal or elevated temperature and, where appropriate, in a closed vessel.

Depending on the process conditions and the starting materials, the end products are obtained in the free form or in the form of their acid addition salts, which are also included in the invention. Thus it is possible to obtain, for example, basic, neutral or mixed salts and, where approprate, also hemihydrates, monohydrates, sesquihydrates or polyhydrates thereof. The acid addition salts of the new compounds can be converted into the free compound in a manner which is in itself known, for example with basic agents such as alkalis or ion exchangers. On the other hand, the resulting free bases can form salts with organic or inorganic acids. In the preparation of acid addition salts, particular use is made of those acids which are suitable for the formation of therapeutically usable salts. The following examples may be mentioned of such acids: hydrogen halide acids, sulphuric acids, phosphoric acids, nitric acid, fumaric acid, aliphatic, alicyclic, aromatic or heterocyclic carboxylic or sulphonic acids, such as formic acid, acetic acid, propionic acid, succinic acid, glycollic acid, lactic acid, malic acid, tartaric acid, citric acid, ascorbic acid, maleic acid or pyruvic acid, benzoic acid, anthranilic acid, p-hydroxybenzoic acid, salicylic acid or embonic acid, methanesulphonic acid, ethanesulphonic acid, hydroxyethanesulphonic acid, ethylenesulphonic acid, halogenobenzenesulphonic acid, toluenesulphonic acid, cyclohexylaminesulphonic acid or sulphanilic acid.

These or other salts of the new compounds, such as, for example, the picrates, can also be used for the purification of the resulting free bases, by converting the free bases into salts, isolating the latter and once more liberating the bases from the salts. Owing to the close relationships between the new compounds in the free form and in the form of their salts, in the preceding and following text the free compounds are also to be understood, where appropriate as the corresponding salts with regard to general sense and intended use.

The invention also relates to those embodiments of the process in which a compound obtained at any stage of the process as an intermediate product is used as a starting material and the missing process steps are carried out, or the process is discontinued at any stage, or a starting material is formed under the reaction conditions, or a reaction component is present in a given case in the form of its salts.

Depending on the choice of starting materials and procedures, the new compounds can be in the form of optical antipodes or racemates or even as mixtures of isomers (mixtures of racemates) provided that they contain at least two asymmetric carbon atoms.

Resulting mixtures of isomers (mixtures of racemates) can be separated, by virtue of the physico-chemical differences of the constituents, into the two stereoisomeric (diastereomeric) pure racemates in a known manner, for example by chromatography and/or fractional crystallisation.

Resulting racemates can be split up into the diastereomers by known methods, for example by recrystallisation from an optically active solvent, with the aid of microorganisms, or by reaction with an optically active acid which forms salts with the racemic compound and by separating the salts obtained in this manner, for example by virtue of their different solubilities, and the antipodes can be liberated from the diastereomers by the action of suitable agents. Particularly customary optically active acids are, for example, the D- and L-forms of tartaric acid, di-o-toluyltartaric acid, malic acid, mandelic acid, camphorsulphonic acid or quinic acid. It is advantageous to isolate the more active of the two antipodes.

It is advantageous to use, for carrying out the reactions according to the invention, those starting materials which give the groups of end products which were particularly mentioned initially and which give, in particular, the end products which have been specially described or singled out.

The starting materials are known or can be obtained, if they are new, by methods which are in themselves known.

Thus the o-nitrobenzoic acid amides of the formula II which have been mentioned as starting materials can be prepared, for example, by first reacting a 5-(halogenosulphonyl)-2-nitrobenzoic acid with a di-lower alkylamine of the formula $(R_1)_2NH$ and then with a halogenating agent, such as a halide of phosphorous acid or sulphurous acid or of sulphuric or phosphoric acid, for example thionyl chloride, and either condensing the resulting 5-(di-lower alkyl sulphamoyl)-2-nitrobenzoyl halide directly with an amine of the formula IV to give an o-nitrobenxoic acid amide of the formula II in the customary manner, for example as described for the reaction of an amine of the formula IV with a functional derivative of a compound of the formula III, or first reacting the resulting 5-(di-lower alkyl sulphamoyl)-2-nitrobenzoyl halide with an amine of the formula

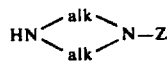

wherein Z represents a lower alkyl radical, above all methyl, and allowing the resulting intermediate product to react further with a compound of the formula VIII, as described for the reaction of compounds of the formulae VII and VIII.

The isatoic acid anhydrides of the formula IIIa, mentioned as starting materials, can be prepared, for example, by reacting a 5-sulphamoylanthranilic acid with a difunctional derivative of carbonic acid, for example with a dihalide, diester or, in particular, an ester-halide thereof, for example with chloroformic acid ethyl ester.

The starting materials of the formula V wherein $R_3$ is hydrogen, can be prepared, for example, by condensing a corresponding 5-sulphamoylanthranilic acid with a functional derivative of acetic acid, for example with acetic anhydride, and either reacting the resulting 6-sulphamoyl-2-methyl-4H-3,1-benzoxazin-4-one directly with an amine of the formula IV in the customary manner, for example as described above for the reaction with a functional derivative of an aminobenzoic compound of the formula III, or first reacting the resulting 6-sulphamoyl-2-methyl-4H-3,1-benzoxazin-4-one with an amine of the formula

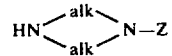

wherein Z is lower alkyl, such as methyl, and allowing the intermediate product obtained in the latter case to react further with a compound of the formula VIII in the customary manner, for example in the manner described for the reaction of compounds of the formulae VII and VIII.

The starting materials of the formulae VI and VII can be prepared by reacting, as described for the reaction with amines of the formula IV, a functional derivative of a compound of the formula III with an amine of the formula

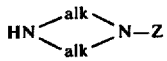

or with an amine of the formula

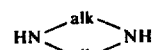

wherein Z is lower alkyl, such as methyl, or by reducing the nitro group in a corresponding 5-sulphamoyl-2-nitrobenzoic acid amide, for example as described for the reduction of compounds of the formula II, and, if necessary, subsequently forming a lower alkyl derivative, for example as described, of a compound of the formula VI which may be obtained and in which $R_3$ is hydrogen.

The new compounds can be used as medicines, for example in the form of pharmaceutical preparations in which they or their salts are present, mixed with a pharmaceutical organic or inorganic, solid or liquid excipient which is suitable, for example, for enternal or parenteral administration. Possible substances for making up the latter are those which do not react with the new compounds, such as, for example, water, gelatine, lactose, starch, magnesium stearate, talc, vegetable oils, benzyl alcohols, gum, polyalkylene glycols, white petroleum jelly, cholesterol or other known medicinal excipients. The pharmaceutical preparations can be, for example, in the form of tablets, dragees, capsules, suppositories, ointments or creme or in liquid form as solutions (for example as an elixir or syrup), suspensions or emulsions. If appropriate, they are sterilised and/or contain auxiliary substances, such as preservatives, stabilisers, wetting or emulsifying agents, salts for modifying the osmotic pressure or buffers. They can also contain other therapeutically valuable substances.

The preparations, which can also be used in veterinary medicine, are obtained according to customary methods. The recommended daily dose per os for a warm-blooded animal weighing about 75 kg is about 15–350 mg.

The following examples illustrate the invention without limiting it, however.

EXAMPLE 1

13.5 g of 5-(dimethylsulphamoyl)-isatoic acid anhydride and 70 ml of absolute dioxane are gently warmed. As soon as the reaction mixture has reached 40°C, a solution of 8.3 g of N-methoxycarbonylpiperazine is added dropwise and the mixture is then heated further, an evolution of carbon dioxide setting in at about 70°C. The mixture is heated under reflux for a further hour and allowed to cool somewhat, insoluble matter is filtered off and the filtrate is concentrated under reduced pressure. The colourless crystals which are precipitated are filtered off with suction and recrystallised from 350 ml of methanol. 13.1 g of 1-[5-dimethylsulphamoyl)-anthraniloyl]-4-ethoxycarbonyl-piperazine, melting point 202°–204°C, are thus obtained.

EXAMPLE 2

1-[5-(Dimethylsulphamoyl)-anthraniloyl]-4-propoxycarbonyl-piperazine, melting point 174°–176°C (from isopropanol/diethyl ether), is obtained by reacting 5-(dimethylsulphamoyl)-isatoic acid anhydride with N-propoxycarbonylpiperazine in a manner analogous to that described in Example 1.

EXAMPLE 3

1-[5-Dimethylsulphamoyl)-anthraniloyl]-4-isobutoxycarbonyl-piperazine, melting point 164°–166°C (from toluene), is obtained by reacting 5-(dimethylsulphamoyl)-isatoic acid anhydride with N-isobutoxycarbonylpiperazine in a manner analogous to that described in Example 1.

EXAMPLE 4

1-[5-(Dimethylsulphamoyl)-anthraniloyl]-4-butoxycarbonyl-piperazine, melting point 175°–177°C (from toluene/isopropanol), is obtained by reacting 5-(dimethylsulphamoyl)-isatoic acid anhydride with N-butoxycarbonylpiperazine in a manner analogous to that described in Example 1.

EXAMPLE 5

1-[5-(Dimethylaminosulphamoyl)-anthraniloyl]-4-methoxycarbonyl-piperazine, melting point 169°–171°C (from methanol), is obtained by reacting 5-(dimethylsulphamoyl)-isatoic acid anhydride with N-methoxycarbonylpiperazine in a manner analogous to that described in Example 1.

EXAMPLE 6

8.1 g of 5-(dimethylsulphamoyl)-isatoic acid anhydride are warmed to 60°–70°C in 80 ml of dioxane. A suspension of 8 g of N-(p-nitrobenzyloxycarbonyl)-piperazine in 80 ml of dioxane is then added and the reaction mixture is heated, evolution of carbon dioxide setting in at about 90°C. The reaction mixture is heated for a further hour under reflux, allowed to cool somewhat and filtered while lukewarm and the filtrate is evaporated to dryness under reduced pressure. The residual oil is boiled up with 70 ml of methanol, whereupon crystallisation takes place. The crystals formed are filtered off with suction and are recrystallised from 250 ml of methanol. 1-[5-(Dimethylsulphamoyl)-anthraniloyl]-4-(p-nitro)-benzyloxycarbonyl-piperazine, melting point 196°–198°C, is thus obtained.

The N-(p-nitrobenzyloxycarbonyl)-piperazine used as starting material can be prepared in the following manner:

32.5 G of N-benzylpiperazine are dissolved in 350 ml of chloroform and 22.2 g of triethylamine and a solution of 43.2 g of chloroformic acid isobornyl ester is added dropwise with stirring; the temperature of the reaction mixture meanwhile must be between 20° and 30°C. The mixture is then stirred for a further 6 hours under reflux and for 8 hours at room temperature and is washed until neutral with 2 N NaOH and the organic phase is separated off, dried over sodium sulphate and evaporated under reduced pressure. The residual oil is distilled, pure 1-benzyl-2-isobornyloxycarbonyl-piperazine passing over at $bp_{1.8} = 220°C$.

43.4 G of 1-benzyl-4-isobornyloxycarbonyl-piperazine are dissolved in 400 ml of ethanol and are hydrogenated at room temperature and normal pressure with the addition of 2.5 g of palladium-charcoal (5% strength) until the absorption of hydrogen is complete. The catalyst is removed by filtration and the solution is evaporated under reduced pressure, N-isobornyloxycarbonyl-piperazine being obtained in the form of a viscous oil which can be used without further purification for the following reaction.

10.0 g of crude N-isobronyloxycarbonyl-piperazine are dissolved in 100 ml of chloroform and 42.2 g of triethylamine and a solution of 8.1 g of chloroformic acid p-nitrobenzyl ester is added dropwise at 20° to 30°C. The mixture is stirred for a further hour at room temperature and for 6 hours under reflux and, after cooling, is washed twice with water, and the organic phase is separated off and dried over sodium sulphate and the solvent is evaporated under reduced pressure, 1-isobornyloxycarbonyl-4-(p-nitrobenzyloxycarbonyl)-piperazine being obtained in the form of a pale yellow oil which can be used without further purification for the following reaction.

46 g of crude 1-isobornyloxycarbonyl-4-(p-nitrobenzyloxycarbonyl)-piperazine are suspended in 140 ml of acetic acid, warmed until a clear solution is formed and allowed to cool to room temperature, when 54 ml of a 30 to 50% strength solution of hydrobromic acid in acetic acid is added and the reaction mixture is at once evaporated under reduced pressure. The crystals obtained are washed four times with diethyl ether and are taken up in a mixture of 50 ml of concentrated sodium hydroxide solution (so-called oil-lye) and 20 ml of 2 N sodium hydroxide solution. The suspension is extracted with three times 200 ml of chloroform and the organic phase is separated off and dried over sodium sulphate and the solvent is evaporated under reduced pressure. The residue is sticky crystals of N-(p-nitrobenzyloxycarbonyl)-piperazine, which can be used without further purification for the reaction which follows or can be converted into the hydrochloride, melting point 218°–221°C, by dissolving in ethyl acetate/ethanol (1:1) and adding a solution of hydrochloric acid in ethyl acetate.

EXAMPLE 7

1-[5-(Dimethylsulphamoyl)-anthraniloyl]-4-benzyloxycarbonyl-piperazine, melting point 156°–161°C (chromatographed on silica gel and recrystallised from methanol), can be obtained in a manner analogous to that described in Example 6, starting from N-isobornyloxycarbonyl-piperazine and chloroformic acid benzyl ester by way of 1-benzyloxycarbonyl-4-isobornyloxycarbonyl-piperazine (melting point of hydrochloride = 128°–130°C (from isopropanol)) and N-benzyloxycarbonylpiperazine by reaction with 5-(dimethylsulphamoyl)-isatoic acid anhydride.

EXAMPLE 8

1-[5-(Dimethylsulphamoyl)-anthraniloyl]-4-allyloxycarbonyl-piperazine, melting point 190°–192°C (from chloroform/ethanol) can also be obtained in a manner analogous to that described in Example 6, starting from N-isobornyloxycarbonylpiperazine and chloroformic acid allyl ester by way of 1-allyloxycarbonyl-4-isobornyloxycarbonyl-piperazine and N-allyloxycarbonyl-piperazine by reaction with 5-(dimethylsulphamoyl)-isatoic acid anhydride.

EXAMPLE 9

35.0 G of the hydrochloride of 1-[5-(dimethylsulphamoyl)-anthraniloyl]-piperazine are shaken with an excess of 5 N sodium hydroxide solution and 300 ml of chloroform until everything has gone into solution. The organic phase is separated off, dried over sodium sulphate and evaporated to dryness under reduced pressure. The resulting 1-[5-(dimethylsulphamoyl)-anthraniloyl]-piperazine is dissolved in 200 ml of absolute chloroform and 14.0 g of diisopropylethyl-amine are added, followed by the dropwise addition of a solution of 11.0 g of chloroformic acid ethyl ester in 50 ml of absolute chloroform. The mixture is stirred overnight at room temperature and washed thoroughly with water and the organic phase is dried over sodium sulphate and evaporated under reduced pressure and the residue is recrystallised from methanol to give 1-[5-dimethylsulphamoyl)-anthraniloyl]4-ethoxycarbonyl-piperazine, melting point 202°–204°C.

The 1-[5-(dimethylsulphamoyl)-anthraniloyl]-piperazine used as starting material, or its hydrochloride, can be prepared in the following manner:

27.0 G of 5-(dimethylsulphamoyl)-isatoic acid anhydride and 18.0 g of N-benzylpiperazine are dissolved in 120 ml of toluene and are heated under reflux for 1 hour. After cooling to room temperature, ethanolic hydrochloric acid is added until a weakly acid reaction is produced and the reation mixture is concentrated under reduced pressure. This gives the crystalline hydrochloride of 1-[5-(dimethylsulphamoyl)-anthraniloyl]-4-benzyl-piperazine, melting point 162°C (decomposition).

40.0 G of the hydrochloride of 1-[5-dimethylsulphamoyl)-anthraniloyl]-4-benzyl-piperazine are dissolved in 320 ml of methanol and, after the addition of 5 g of 5% strength palladium-charcoal, are hydrogenated at 15°–25°C and normal pressure until the absorption hydrogen is complete. The catalyst is filtered off and the solution is evaporated under reduced pressure to give the crystalline hydrochloride of 1-[5-(dimethylsulphamoyl)-anthranyloyl]-piperazine, melting point 271°–272°C.

EXAMPLE 10

1-[5-(Dimethylsulphamoyl)-anthraniloyl]-4-propoxycarbonyl-piperazine, melting point 174°–176°C (from isopropanol/ether), can also be prepared in a manner analogous to that described in Example 9, starting from 1-[5-(dimethylsulphamoyl)-anthraniloyl]-piperazine or its hydrochloride by reaction with chloroformic acid propyl ester.

EXAMPLE 11

1-[5-(Dimethylsulphamoyl)-anthraniloyl]-4-isopropoxycarbonyl-piperazine, melting point 164°–166°C (from toluene), can also be prepared in a manner analogous to that described in Example 9, starting from 1-[5-(dimethylsulphamoyl)-anthraniloyl]-piperazine or its hydrochloride by reaction with chloroformic acid isopropyl ester.

EXAMPLE 12

1-[5-(Dimethylsulphamoyl)-anthraniloyl]-4-butoxycarbonylpiperazine, melting point 175°–177°C (from toluene/isopropanol), can also be prepared in a manner analogous to that described in Example 9, starting from 1-[5-(dimethylsulphamoyl)-anthraniloyl)]-piperazine or its hydrochloride by reaction with chloroformic acid butyl ester.

EXAMPLE 13

1-[5-(Dimethylsulphamoyl)-anthraniloyl]4-methoxycarbonyl-piperazine, melting point 169°–171°C (from methanol), can also be prepared in a manner analogous to that described in Example 9, starting from 1-[5-(dimethylsulphamoyl)-anthraniloyl]-piperazine or its hydrochloride by reaction with chloroformic acid methyl ester.

EXAMPLE 14

1-[5-(Dimethylsulphamoyl)-anthraniloyl-4-(p-nitro)benzyloxycarbonyl-piperazine, melting point 196°–198°C (from methanol), can also be prepared in a manner analogous to that described in Example 9, starting from 1-[5-(dimethylsulphamoyl)-anthraniloyl]-piperazine or its hydrochloride by reaction with chloroformic acid p-nitro-benzyl ester.

EXAMPLE 15

1-[5-(Dimethylsulphamoyl)-anthraniloyl]-4-benzyloxycarbonyl-piperazine, melting point 156°–161°C (from methanol), can also be prepared in a manner analogous to that described in Example 9, starting from 1-[5-(dimethylsulphamoyl)-anthraniloyl]-piperazine or its hydrochloride by reaction with chloroformic acid benzyl ester.

EXAMPLE 16

1-[5-(Dimethylsulphamoyl)-anthraniloyl]-4-allyloxycarbonyl-piperazine, melting point 190°–192°C (from chloroform/ethanol), can also be prepared in a manner analogous to that described in Example 9, starting from 1-[5-(dimethylsulphamoyl)-anthraniloyl]-piperazine or its hydrochloride by reaction with chloroformic acid allyl ester.

EXAMPLE 17

14 G of 1-[5-(dimethylsulphamoyl)-anthraniloyl]-4-ethoxycarbonyl-piperazine and 6.3 g of triethyl oxonium tetrafluoroborate are dissolved in 250 ml of absolute chloroform and are heated under reflux overnight. After cooling, ammonia is added and the mixture is shaken thoroughly. The organic phase is separated off, washed with water, dried over sodium sulphate and evaporated to dryness under reduced pressure. The residue is chromatographed on aluminium oxide (neutral, grade I activity) and the resulting crystals are recrystallised from ethanol. This gives 1-[5-(dimethylsulphamoyl)-N-ethyl-anthraniloyl]-4-ethoxycarbonyl-piperazine, melting point 167°–168°C.

EXAMPLE 18

The following compounds can also be prepared in a manner analogous to that of Examples 1, 6, 20 and 9: 1-[5-(Dimethylsulphamoyl)-anthraniloyl]-4-acetylpiperazine, melting point 201°–202°C, 1-[5-(dimethylsulphamoyl)-anthraniloyl]4-propionylpiperazine, melting point 161°–163°C and 1-[5-(dimethylsulphamoyl)-anthraniloyl]4-benzoylpiperazine, melting point 207°–209°C.

EXAMPLE 19

A charge is made up of 5g of the hydrochloride of 1-[5-(dimethylsulphamoyl)-anthraniloyl]-piperazine (prepared as described in Example 9), 4.1 g of diisopropylethylamine and 80 ml of chloroform. A solution of 2.2 g of phenylacetyl chloride in 20 ml of chloroform is then added dropwise. Stirring of the clear solution is continued overnight. The reaction solution is then diluted with chloroform and is washed once with 150 ml of icecold 2 N hydrochloric acid and once with the same quantity of water. The chloroform solution is dried over sodium sulphate and evaporated under reduced pressure. The crude product is recrystallised twice from isopropanol. This gives 1-[5-(dimethylsulphamoyl)-anthraniloyl]4-phenylacetyl-piperazine, melting point 174°–176°C.

EXAMPLE 20

0.4 G of 1-[5-(dimethylsulphamoyl)-2-nitrobenzoyl]-4-ethoxycarbonyl-piperazine is dissolved in 30 ml of ethanol and is hydrogenated in the presence of 50 mg of palladiumcharcoal until the absorption of hydrogen is complete. The ethanol solution is filtered from the catalyst and evaporated in vacuo and the residue is recrystallised from methanol. This gives 1-[5-(dimethylsulphamoyl)-anthraniloyl]-4-ethoxycarbonyl-piperazine, melting point 202°–204°C.

The 1-[5-dimethylsulphamoyl)-2-nitrobenzoyl]-4-ethoxycarbonyl-piperazine used as the starting material can be prepared in the following manner:

7.1 G of 1-[5-(dimethylsulphamoyl)-2-nitrobenzoyl]-4-methylpiperazine are dissolved in 500 ml of chloroform and heated. 1.08 g of chloroformic acid ethyl ester are added dropwise to this boiling solution and the mixture is heated under reflux, further additions of 1.08 g of chloroformic acid ethyl ester being made each time after 4.5, 22 and 29 hours. After 45 hours, the suspension is filtered while hot and the filtrate is evaporated to dryness. The residue is dissolved in methylene chloride and purified by chromatography on a 40-fold quantity of silica gel. 1-[5-(Dimethylsulphamoyl)-2-nitrobenzoyl]-4-ethoxycarbonyl-piperazine, melting point 139°–143°C, is eluted by means of methylene chloride. The product can be used further without additional purification.

EXAMPLE 21

3.4 G of 1-[5-(dimethylsulphamoyl)-2-acetamidobenzoyl]-4-ethoxycarbonylpiperazine are dissolved in 100 ml of ethanol and 6 ml of 15% strength sodium hydroxide solution are added. The solution is allowed to stand for 2–3 days at 20°C and the methanol is then evaporated off over the course of 2 hours in a slight vacuum at a bath temperature of approx. 60°C. The residual aqueous solution is diluted with a little water and extracted by shaking with methylene chloride. The combined organic extracts are dried over sodium sulphate and evaporated to dryness in vacuo. An oil is obtained which rapidly solidifies. This oil is dissolved in a mixture of equal parts of methylene chloride and acetone and is filtered through a 10-fold quantity of silica gel. The filtrate is evaporated and the residue is recrystallised from methanol. This gives 1-[5-(dimethylsulphamoyl)-anthranoyl]-4-ethoxycarbonylpiperazine, melting point 202°–203°C.

The starting material can be prepared as follows: A solution of 7.9 g of N-ethoxycarbonylpiperazine in 80 ml of dioxane is slowly added dropwise, with stirring, to a boiling solution of 13 g of anhydro-(n-acetyl-5-dimethylsulphamoyl)-anthranilic acid in 100 ml of dioxane, and the solution is heated to the boil for a further 10 hours. The reaction mixture is evaporated and the crude 1-[5-(dimethylsulphamoyl)-2-acetoamido-benzoyl]-4-ethoxycarbonylpiperazine, melting point 245°–248°C, is used direct for further reaction.

EXAMPLE 22

Tablets containing 250 mg of active substance can be prepared, for example, in the following composition:

Composition per tablet

| | |
|---|---:|
| 1-[5-(Dimethylsulphamoyl)-anthraniloyl]-4-ethoxycarbonyl-piperazine hydrochloride | 250.0 mg |
| Mannitol | 60.0 mg |
| Wheat starch | 91.0 mg |
| Gelatine | 4.0 mg |
| Talc | 13.0 mg |
| Magnesium stearate | 2.0 mg |
| | 420.0 mg |

PREPARATION

The 1-[5-(dimethylsulphamoyl)-anthraniloyl]-4-ethoxycarbonyl-piperazine hydrochloride is mixed with the mannitol and a part of the wheat starch and the mixture is forced through a sieve. The gelatine is dissolved in a 5-fold quantity of water on the water bath and the powder mixture is kneaded with the solution until a plastic composition has been formed. This composition is forced through a sieve of approx. 3 mm mesh width and dried and the dried granules are once more forced through a sieve. The remaining wheat starch, talc and magnesium stearate are then mixed in. The resulting mixture is pressed into tablets of 420 mg (with a breaking groove).

What we claim is:

1. A 2-amino-5-sulphamoylbenzoic acid amide of the general formula

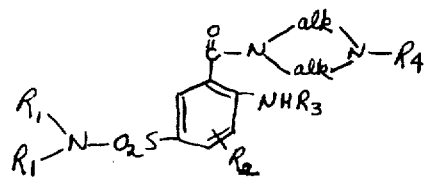

wherein $R_1$ denotes identical lower alkyl groups with 1 to 4 C atoms, $R_2$ denotes hydrogen, lower alkyl or lower alkoxy with up to 4 C atoms or halogen up to atomic number 17, $R_3$ denotes hydrogen, hydroxyl or lower alkyl with 1 to 4 C atoms, $R_4$ denotes a group of the formula —COOR' or —COR' wherein R' denotes lower alkyl with 1 to 4 C atoms, lower alkenyl with 3 or 4 C atoms or phenyl, benzyl or phenylethyl which are optionally monosubstituted or disubstituted in the phenyl part by lower alkyl or lower alkoxy with 1 to 4 C atoms in each case, halogen up to atomic number 17 or nitro, and alk denotes 1,2-alkylene with 2–4 C atoms.

2. The compound of claim 1 of the general formula I wherein $R_1$ is methyl, $R_2$ is hydrogen, $R_3$ is hydrogen, ethyl or methyl, $R_4$ is a group of the formula —COOR' or —COR' wherein R' denotes lower alkyl with 1 to 4 C atoms, allyl, phenyl or benzyl which is optionally nitrated, and alk is propylene-1,2 or ethylene.

3. The compound of claim 1 of the general formula I wherein $R_1$ is methyl, $R_2$ is hydrogen, $R_3$ is hydrogen or ethyl, $R_4$ is a group of the formula —COOR' wherein R' denotes lower alkyl with 1 to 4 C atoms, allyl or benzyl which is optionally nitrated in the p-position, and alk is ethylene.

4. The compound of claim 1 being 1-[5-(Dimethylsulphamoyl)-anthraniloyl]-4-ethoxycarbonyl-piperazine or a therapeutically acceptable acid addition salt thereof.

5. The compound of claim 1 being 1-[5-(Dimethylsulphamoyl-anthraniloyl]-4-propoxycarbonyl-piperazine or a therapeutically acceptable acid addition salt thereof.

6. The compound of claim 1 being 1-[5-(Dimethylsulphamoyl)-anthraniloyl]-4-isobutoxycarbonyl-piperazine or a therapeutically acceptable acid addition salt thereof.

7. The compound of claim 1 being 1-[5-(Dimethylsulphamoyl)-anthraniloyl]-4-butoxycarbonyl-piperazine or a therapeutically acceptable acid addition salt thereof.

8. The compound of claim 1 being 1-[5-(Dimethylaminosulphamoyl)-anthraniloyl]-4-methoxycarbonyl-piperazine or a therapeutically acceptable acid addition salt thereof.

9. The compound of claim 1 being 1-[5-(Dimethylsulphamoyl)-anthraniloyl]-4-(p-nitro)-benzyloxycarbonyl-piperazine or a therapeutically acceptable acid addition salt thereof.

10. The compound of claim 1 being 1-[5-(Dimethylsulphamoyl)-anthraniloyl]-4-benzyloxycarbonyl-piperazine or a therapeutically acceptable acid addition salt thereof.

11. The compound of claim 1 being 1-[5-(Dimethylsulphamoyl)-anthraniloyl]-4-allyloxycarbonyl-piperazine or a therapeutically acceptable acid addition salt thereof.

12. The compound of claim 1 being 1-[5-(Dimethylsulphamoyl)-N-ethyl-anthraniloyl]-4-ethoxycarbomyl-piperazine or a therapeutically acceptable acid addition salt thereof.

13. The compound of claim 1 being 1-[5-(Dimethylsulphamoyl)-anthraniloyl]-4-acetyl-piperazine or a therapeutically acceptable acid addition salt thereof.

14. The compound of claim 1 being 1-[5-(Dimethylsulphamoyl)-anthraniloyl]-4-propionylpiperazine or a therapeutically acceptable acid addition salt thereof.

15. The compound of claim 1 being 1-[5-(Dimethylsulphamoyl)-anthraniloyl]-4-phenyl-acetyl piperazine or a therapeutically acceptable acid addition salt thereof.

16. The compound of claim 1 being 1-[5-(Dimethylsulphamoyl)-anthraniloyl]-4-benzoylpiperazine or a therapeutically acceptable acid addition salt thereof.

* * * * *